United States Patent [19]
Fentress et al.

[11] Patent Number: 5,271,745
[45] Date of Patent: Dec. 21, 1993

[54] MEDICAL TUBING RETAINING DEVICE AND METHOD OF USE

[75] Inventors: Philip W. Fentress, Lake Forest, Ill.; Richard P. Shepard, Wauwatosa, Wis.; Susan B. Fentress, Lake Forest, Ill.

[73] Assignee: Tabex Industries, Inc., Grayslake, Ill.

[21] Appl. No.: 967,175

[22] Filed: Oct. 27, 1992

[51] Int. Cl.$^5$ .............................................. A61M 5/31
[52] U.S. Cl. ........................ 604/179; 128/DIG. 26
[58] Field of Search ................ 604/174, 179, 180; 128/DIG. 26, DIG. 6

[56] References Cited

U.S. PATENT DOCUMENTS

| | | | |
|---|---|---|---|
| D. 292,127 | 9/1987 | Aiello | D24/58 |
| 3,726,280 | 4/1973 | Lacount | 128/DIG. 26 |
| 3,765,421 | 10/1973 | Poprik | 128/DIG. 26 |
| 4,308,642 | 1/1982 | Heyman | 128/DIG. 26 |
| 4,445,894 | 5/1984 | Kovacs | 604/179 |
| 4,490,141 | 12/1984 | Lacko et al. | 604/180 |
| 4,534,762 | 8/1985 | Heyer | 604/180 |
| 4,582,508 | 4/1986 | Pavelka | 604/179 |
| 4,596,560 | 6/1986 | Simpson | 604/174 |
| 4,665,566 | 5/1987 | Garrow | 128/DIG. 26 |
| 4,666,432 | 5/1987 | McNeish et al. | 604/179 |
| 4,700,432 | 10/1987 | Fennell | 24/160 |
| 4,738,661 | 4/1988 | Marut | 604/179 |
| 4,799,923 | 1/1989 | Campbell | 604/179 |
| 4,911,178 | 3/1990 | Neal | 128/802 |
| 4,955,867 | 9/1990 | Endo | 604/179 |
| 5,048,512 | 9/1991 | Turner et al. | 604/179 |

OTHER PUBLICATIONS

CAPD Waist Carrying Pouch (Baxter).
Cath-Secure (MC. Johnson Co, Inc).

*Primary Examiner*—Paul J. Hirsch
*Attorney, Agent, or Firm*—Susan B. Fentress

[57] ABSTRACT

This invention relates to a medical tubing retaining device and method to use the same. More particularly, it relates to a one piece flexible band containing members to form a sling. The sling is of sufficient length to retain coiled medical tubing when affixed to the band. This device is used to retain tubing from indwelling devices such as catheters.

6 Claims, 3 Drawing Sheets

MEDICAL TUBING RETAINING DEVICE AND METHOD OF USE

BACKGROUND OF THE INVENTION

Field of the Invention: This invention relates to medical tubing retaining devices and more particularly to a one-piece band forming a sling to retain coiled medical tubing that extends outwardly from or along a patient's body.

Description of the Prior Art: Certain types of medical devices, such as indwelling catheters and other access tubes, are implanted into a patient's abdomen, chest cavity, stomach, blood vessel or the like. These devices sometimes include tubing and in the case of a peritoneal dialysis catheter, project outwardly from the implanted medical device relative to the skin. Patients have to contend with somehow immobilizing this medical tubing that may vary in length, according to the treatment protocol, from about 12 inches to about 30 inches and may include the use of extension or transfer sets for fluid infusion or drainage. The skin exit site is also susceptible to pulling, tugging or other tractions on the catheter or tubing. To avoid problems a patient may typically roll up and tape the catheter and transfer set to the surrounding skin.

To avoid taping the medical device to the patient's skin, certain garments, including means to hold indwelling catheters, have been disclosed. See, e.g., Pavelka, U.S. Pat. No. 4,582,508 and McNeish et al., U.S. Pat. No. 4,666,432. These garments consist of several components such as straps and pockets. In these garments the tubing is threaded through a hole and is retained in a pocket. None of these garments, however, is commercially available; presumably, they are not available because of cost to manufacture multi-component garments and the difficulty of use associated with threading tubing through a hole into a pocket. The present one piece device solves the aforementioned problems by providing a sling to retain the coiled medical tubing.

SUMMARY OF THE INVENTION

The present invention provides a retaining device for coiled medical tubing, a portion of which extends outwardly from or along a patient's body. The device is comprised of a one piece flexible band with means to secure the band around the abdomen of a patient without contacting the patient's skin with the affixing means. The band forms a sling of sufficient size to hold the coiled medical tubing.

More particularly this invention provides a one piece flexible band with means to secure the band around the abdomen of the patient without contacting the patient's skin containing at least one flap with means to affix the distal end of the flap to the band, the flap being of sufficient length to retain the coiled medical tubing. Additionally this invention provides a one piece flexible band with means to secure the band around the abdomen of a patient without contacting the patient's skin with affixing means, the band containing at least two flaps on the same side of the band forming a slot to receive the proximal end of the medical tubing and means to affix the distal end of at least one flap to the band, the flaps being of sufficient length when affixed to the band to retain the coiled medical tubing.

This invention also provides a method to use this device to retain coiled medical tubing.

DETAILED DESCRIPTION OF THE INVENTION

Figure 1:
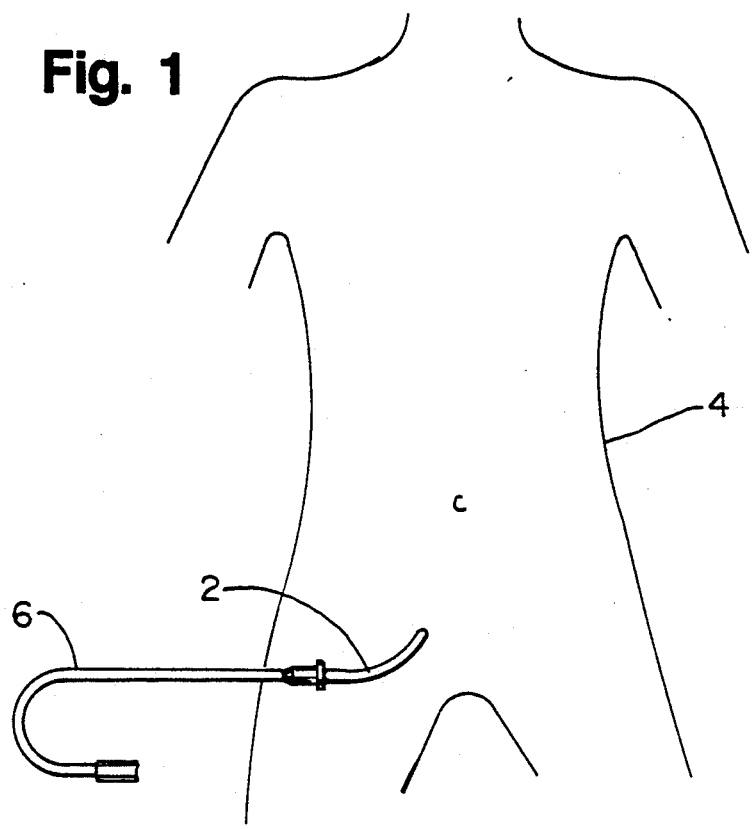
FIG. 1 shows a schematic drawing of an indwelling catheter and transfer set.

Now referring to FIG. 1 a catheter 2 projects outwardly from patient's body 4. Transfer set, i.e. medical tubing, 6 is attached to catheter 2.

Figure 2A:
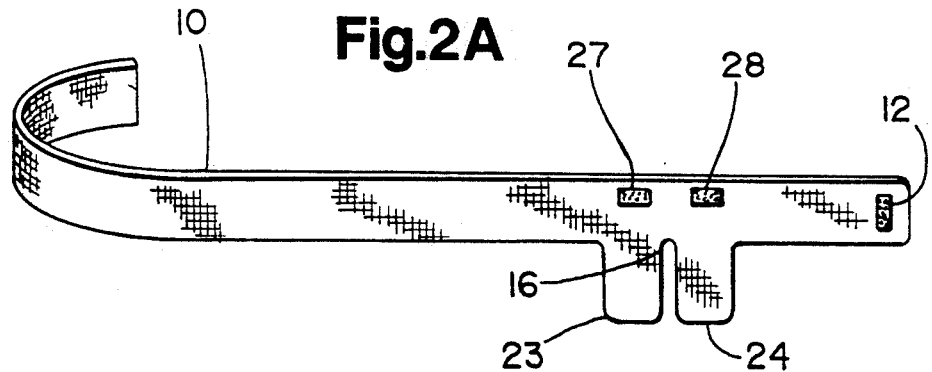
FIG. 2A shows a schematic drawing of an embodiment of the one piece medical tubing retaining device.
Figure 2B:
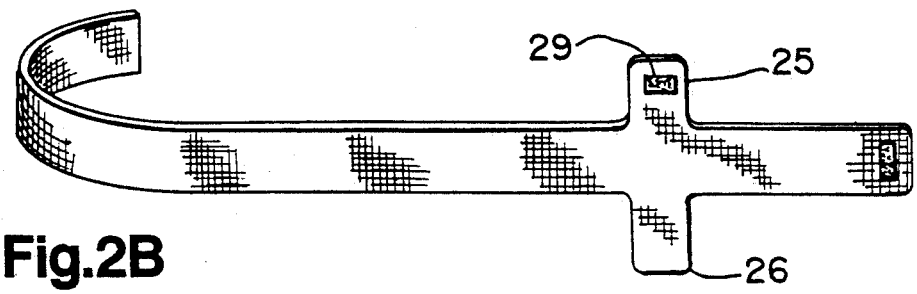
FIG. 2B shows a schematic drawing of an embodiment of the one piece medical tubing retaining device.

In FIG. 2A and 2B embodiments of the medical tubing retaining device are shown. FIG. 2A shows a one piece band 10 having affixing means 12 at the end of the band to secure the band around the abdomen of a patient 4. The affixing means may be adhesive, hook-and-loop material such as VELCRO (Velcro Industries, B.V.) or a hook-and-eye, etc. The one piece band 10 can be made of woven fabric or paper but preferably is of a non-woven fabric such as SONTARA (DuPont), or NOVONETTE or FLEXILON (Veratec Div. International Paper). The band 10 contains two flaps in this embodiment In FIG. 2A flaps 23 and 24 are on the same side of the band and form a slot 16. The slot 16 is used to locate the band 10 with reference to the catheter 2. Affixing means 27 and 28 can be located on the band 10 to affix the flaps to said band or the affixing means can be located on flaps 23 and 24. These affixing means can be adhesive, VELCRO or hook-and-eye, etc. The flaps are then affixed to the band or to the upper portion of the flaps. Affixing means 12, 27 and 28 may be substantially round in shape such as circular or star shaped, or substantially square such as rectangular, square or trapezoidal so as to eliminate the need to orient the application of rectangular or irregularly shaped affixing means during manufacturing and assembly of the device.

Figure 3:
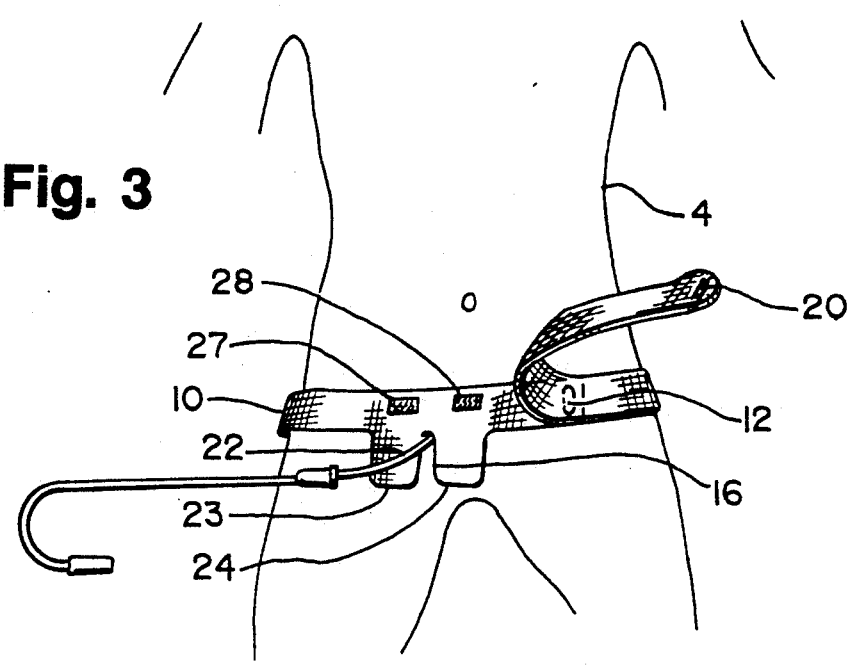
FIG. 3 shows a schematic drawing of the embodiment of the one piece medical tubing retaining device shown in FIG. 2A and medical tubing.

In embodiment 2B the flaps 25 and 26 are located on opposite sides of the band. Affixing means 29 is located on one flap 25 or 26 to affix the flaps 25 and 26 together to retain the medical tubing 6. The flaps 23,24,25 and 26 are of sufficient length to retain the coiled medical tubing 30 when they are affixed Now referring to FIG. 3, the one piece medical tubing retaining device shown in FIG. 2A is secured around the abdomen of a patient 4 using affixing means 12. In this particular embodiment an adhesive patch 12 on one end of the band 10 adheres to another part of the band to secure the band around the abdomen of a patient 4. Additionally, the other end of the band may also include an adhesive patch 20 to secure the unused portion of the band 10. The adhesive patch 20 may be located on the reverse side of the band 10.

Figure 4:
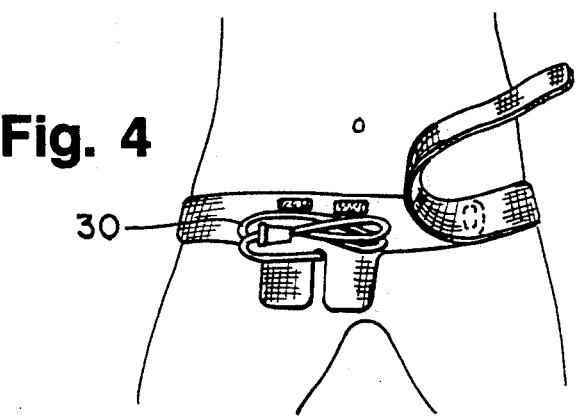
FIG. 4 shows a schematic drawing of an embodiment of the one piece medical tubing retaining device shown in FIG. 2A and coiled medical tubing.
Figure 5A:
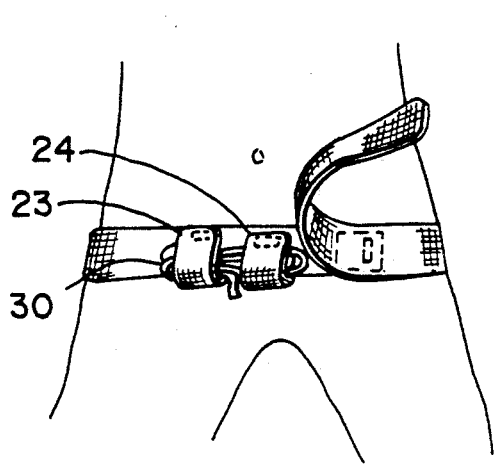
FIG. 5A shows a schematic drawing of an embodiment of medical tubing retained in the one piece device shown in FIG. 2A retaining coiled medical tubing.
Figure 5B:
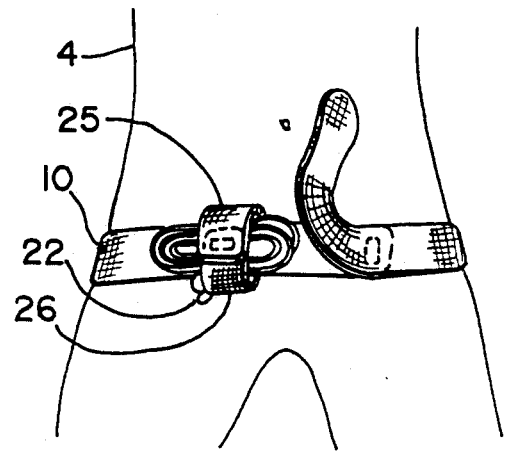
FIG. 5B shows a schematic drawing of an embodiment of medical tubing retained in the one piece device shown in FIG. 2B retaining coiled medical tubing

The band 10 is located by placing slot 16 around the proximal end 22 of the medical tubing outside of the patient's body 4. The band 10 contains affixing means 27 and 28 to affix the distal ends of flaps 23 and 24 to band 10. Alternatively, affixing means 27 and 28 may be located on the distal ends of flaps 23 and 24. In FIG. 4, the medical tubing is coiled 30 and in FIG. 5A the flaps 23 and 24 are affixed to band 10 to retain the coiled medical tubing 30. When the flaps are affixed to the band they form a sling. Alternatively, in FIG. 5B if the flaps 25 and 26 are located on opposite sides of the band 10, the band is located on body 4 by placing the corner formed by the lower edge of band 10 and edge of flap 26 adjacent to the proximal end 22 of the medical tubing outside of the patient's body 4. The flaps 25 and 26 are then affixed to each other to retain the coiled medical tubing 30. Flaps 23, 24, 25 and 26 may be triangularly shaped to accommodate the use of round or spotlike affixing means without leaving the corners of the flaps loose after affixing to band 10.

Figure 6A:
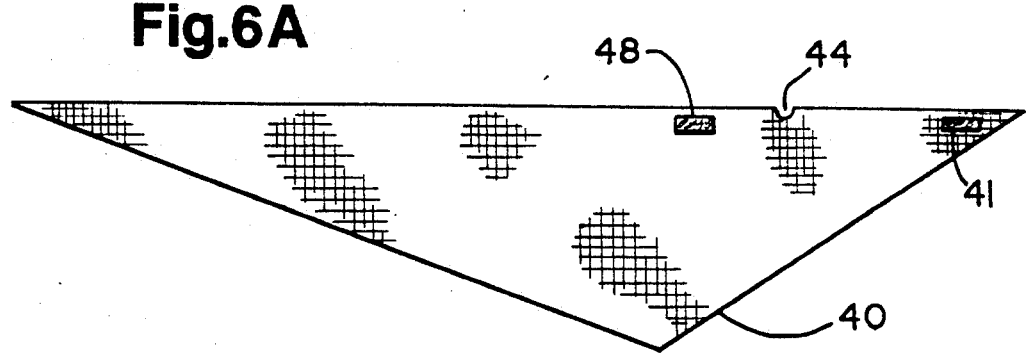
FIG. 6A shows a schematic drawing of an embodiment of the medical tubing retaining device.
Figure 6B:
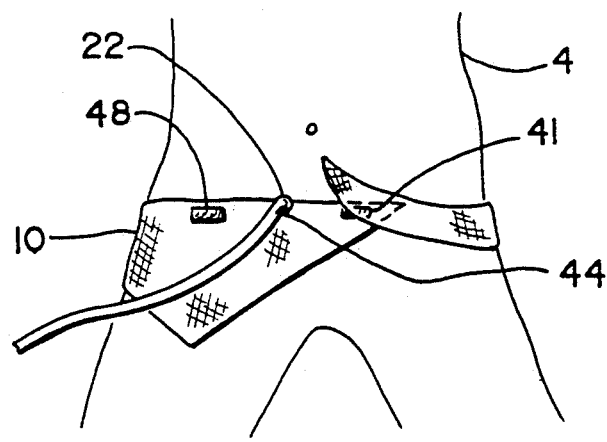
FIG. 6B shows a schematic drawing of an embodiment of the medical tubing retaining device shown in FIG. 6A in position on the patient's abdomen.
Figure 6C:
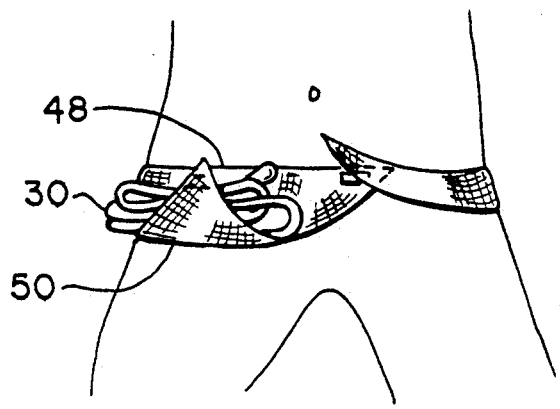
FIG. 6C shows a schematic drawing of an embodiment of the medical tubing retaining device shown in FIG. 6A retaining coiled medical tubing.

In yet another embodiment shown in FIGS. 6A, 6B and 6C a flexible one piece band having a "scarf" shape 40 is secured around the patient's abdomen 4 by affixing means 41. The band 10 in this embodiment is located by placing the proximal end of the medical tubing 22 outside of the patient's body 4 into notch 44 in the central area of band 10. The medical tubing is retained by affixing means 48 to the band 10. The affixing means can be VELCRO, adhesive, hook-and-eye, etc. The notch 44 is offset from the affixing means 48 to affix to band 10 in a sling 50 so to retain the coiled medical tubing 30.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the practice in the field to which the invention pertains, or as are obvious to persons skilled in the field.

We claim:

1. A retaining device for coiled medical tubing, a portion of which extends outwardly from or along a person's body, the device comprising:
   (a) a flexible band with affixing means to secure said band around the abdomen of a patient, without contacting patient's skin with said affixing means,
   (b) said band containing at least two flaps of sufficient length to retain said coiled medical tubing, said flaps forming a slot to receive the proximal end of said medical tubing outside of the body, with means to affix the distal end of said flaps to said band to retain said coiled medical tubing.

2. The retaining device of claim 1 wherein said band includes an affixing means on the distal end of said band to retain unused portion of said band when the band is secured around the abdomen of a patient.

3. The retaining device of claim 1 wherein said affixing means are substantially round adhesive patches.

4. The retaining device of claim 1 wherein said affixing means are substantially square adhesive patches.

5. A retaining device for coiled medical tubing, a portion of which extends outwardly from or along a person's body, the device comprising:
   (a) a one piece flexible band with means to secure said band around the abdomen of a patient said band integral with a sling with affixing means distal to said band, said sling being of sufficient size to hold said coiled medical tubing when said sling is affixed to said band, said band containing a notch in a top edge to locate said coiled medical tubing.

6. A method to retain medical tubing, a portion of which extends outwardly from or along a patient's body comprising:
   (a) locating said medical tubing with reference to a said retaining device as recited by claim 1;
   (b) coiling said medical tubing;
   (c) affixing said flaps of said device to said band to retain the coiled medical tubing.

* * * * *